United States Patent [19]

Domino

[11] Patent Number: 4,888,015

[45] Date of Patent: Dec. 19, 1989

[54] METHOD OF REPLACING AN EYE LENS

[76] Inventor: Rudolph S. Domino, 228 Plainfield Ave., Edison, N.J. 08817

[21] Appl. No.: 409,865

[22] Filed: Aug. 20, 1982

[51] Int. Cl.⁴ .......................... A61F 2/16; A61B 17/00; A61B 17/28
[52] U.S. Cl. ........................................ 623/6; 606/107; 606/210
[58] Field of Search .................... 3/13; 128/354, 321, 128/303 R; 623/6

[56] References Cited

U.S. PATENT DOCUMENTS

| | | | |
|---|---|---|---|
| 896,338 | 8/1908 | Tolman | 128/354 |
| 1,725,173 | 8/1929 | Anderson | 128/354 X |
| 3,553,299 | 1/1971 | Thiele et al. | 623/6 |
| 4,213,460 | 7/1980 | Weiner | 128/303 R |
| 4,242,762 | 1/1981 | Tennant | 623/6 |
| 4,253,199 | 3/1981 | Banko | 623/6 |
| 4,285,073 | 8/1981 | Szycher | 623/6 |
| 4,316,292 | 2/1982 | Alexeev | 623/6 |
| 4,409,691 | 10/1983 | Levy | 623/6 |
| 4,418,431 | 12/1983 | Feaster | 623/6 |
| 4,449,257 | 5/1984 | Koeniger | 623/6 |

FOREIGN PATENT DOCUMENTS 570363  8/1977  U.S.S.R. .................... 623/6

Primary Examiner—Ronald L. Frinks
Attorney, Agent, or Firm—Lerner, David, Littenberg, Krumholz & Mentlik

[57] ABSTRACT

A method of replacing a human or animal lens is disclosed, along with a tool for use in such procedure and a flexible lens for use as an implant or transplant. The procedure includes the use of a horizontal capsulotomy incision to allow for the removal of the lens from the lens capsule without destruction or removal of any portion of the capsule. No sutures or other unnatural materials are required. A special tool for use in this procedure is disclosed which includes saucer-shaped gripping members which can grip and loosen the lens from the lens capsule and keep the capsule open during the transplant. The implanted lens, which may be of a soft material having a variable focus, is formed from an inert, non-toxic material. When a natural lens or a flexible artificial lens is utilized in the procedure, the natural constriction and relaxation of the ciliary muscles allows for the variation of the focus of the lens in a manner which closely approximates that of the original natural lens.

15 Claims, 3 Drawing Sheets

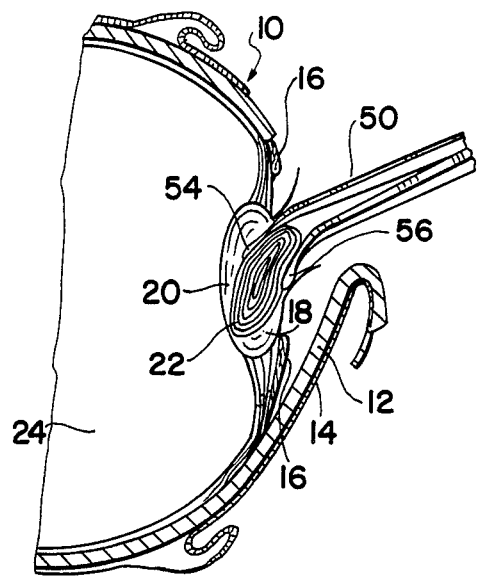
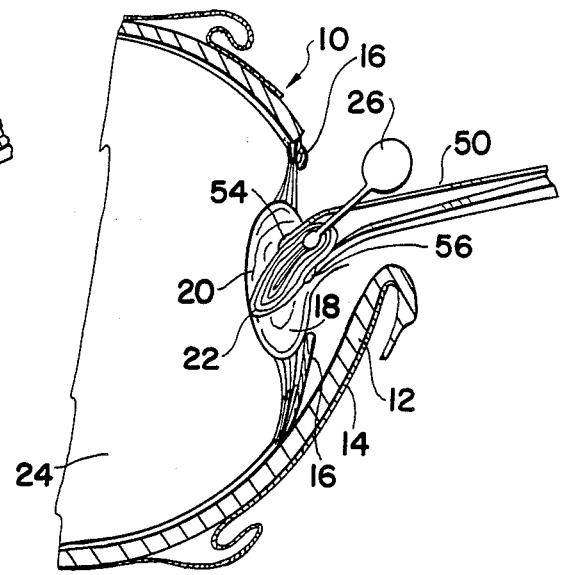
FIG. 1  FIG. 2
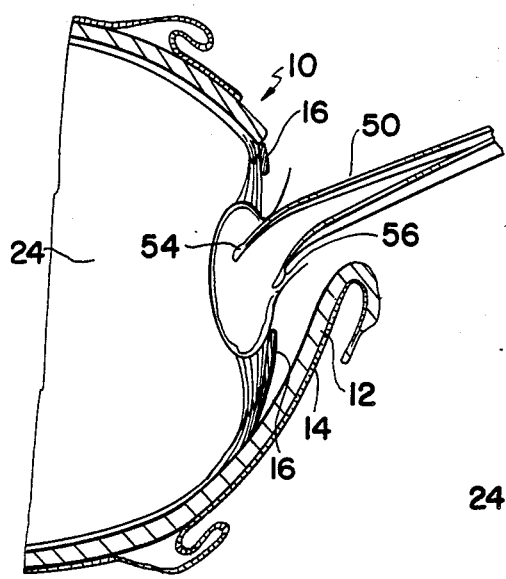
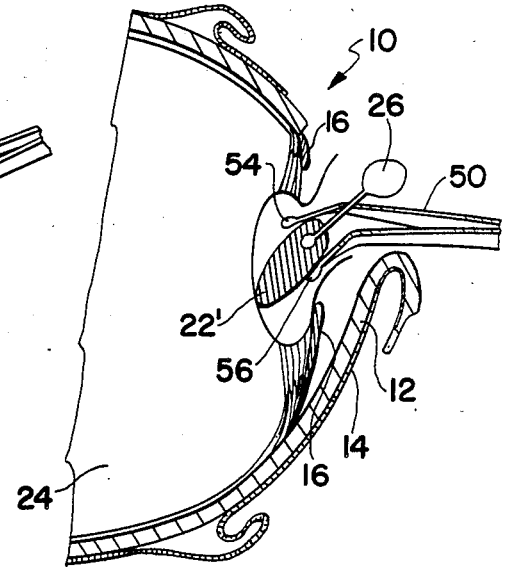
FIG. 3  FIG. 4

METHOD OF REPLACING AN EYE LENS

FIELD OF THE INVENTION

The present invention relates to intraocular lenses and more particularly to a new system for surgically removing a damaged lens and replacing it with a new lens. The present invention also relates to a new tool for use in such procedure as well as a new variable focus lens which can be implanted in an eye.

BACKGROUND OF THE INVENTION

There has long been a need for a satisfactory method of replacing the lens of a human or animal eye which has been damaged, through cataracts or other disease or accident. There have been numerous attempts to develop a procedure which is relatively safe and simple, which minimizes trauma to the eye, and which results in materially improved vision under a variety of conditions.

For example, U.S. Pat. No. 4,253,199 to Anton Banko discloses various methods and apparatus for eye implants within the posterior chamber of the eye. In the procedure taught by Banko, the entire anterior portion of the lens capsule is apparently removed and, in some cases, the posterior portion of the lens capsule was also removed. An implant of the capsule is attached to the ciliary body by means of sutures. In the Banko procedure, there is considerable trauma to the eye, in that essentially the entire lens capsule is destroyed and removed.

Another prior approach is illustrated in U.S. Pat. Nos. 4,254,509 and 4,261,065 to Jerald L. Tennant. These patents disclose a lens implant which is positioned in the anterior chamber of the eye and not within the location previously occupied by the natural lens. In both of these patents, it appears that the natural lens as well as the entire lens capsule have been totally removed.

U.S. Pat. No. 4,242,762, also in the name of Jerald L. Tennant discloses an implant within the lens capsule, whereby a triangular opening is formed in the anterior capsule. Similarly, in U.S. Pat. No. 4,243,510, also in the name of Jerald L. Tennant, the jagged margins represent an opening made in the lens capsule for fragmentation and removal of the lens. In both of these patents, at least part of the anterior portion of the lens capsule is destroyed in the process of replacing the lens.

U.S. Pat. No. 4,251,887 in the name of Aziz Y. Anis discloses an intracapsular implant in which a triangular capsulectomy (that is, a removal of a portion of the capsule) is performed and there is inserted within the eye a lens with two side loops, each of which forms the shape of a kidney. Here again, a portion of the capsule is irrevocably removed and destroyed and, additionally, foreign substances are placed in the eye.

In U.S. Pat. No. 4,002,169, there is disclosed a surgical method whereby a tool is inserted into the lens and probes are used to "masticate" the contents of the lens capsule. Suction is then used to withdraw the contents of the capsule. The interior of the capsule is then flushed and cleaned and a lens filler such a silicone is then inserted through the tool. All of this is accomplished through a thin needle. This procedure, while retaining the lens capsule, does not lend itself to the insertion of a new lens having a predetermined shape and most certainly could not be used to insert a live lens transplant.

Russian Inventor's Certificate No. 572,267 to Alekseev appears to disclose a method of implanting an artificial crystalline lens. It appears that, through an unspecified special device, a capsulectomy (that is, removal of a portion of a capsule) is performed in the anterior area. The nucleus and crystalline masses are removed through a "round orifice" in the anterior capsule, and an intraocular lens of up to five millimeters in diameter is implanted into the crystalline bursa. Since a natural lens is substantially larger, it appears that Alekseev only removes the central five millimeters of the lens and replaces it with an implant. This essentially only replaces that portion of the lens which is aligned with the pupil. This procedure, like the others, poses certain disadvantages, including the fact that if a lens is diseased, removal of only a portion of the lens could result in continued problems after the surgical procedure.

Accordingly, it is an object of the present invention to provide a new technique for a lens implant.

It is a further object of the present invention to provide such a lens implant which minimizes trauma to the eye.

It is another object of the present invention to provide such a lens implant which leaves the lens capsule substantially intact.

It is an additional object of the present invention to provide such a lens implant which replaces a diseased lens with a lens having substantially identical optical characteristics.

It is still another object of the present invention to provide such a lens implant which responds to the natural muscular movement of the eye to vary the focus of the lens under different conditions.

It is still a further object of the present invention to provide a lens implant in which the entire diseased lens is removed and replaced.

It is an additional object of the present invention to provide such a lens implant in which the newly implanted lens is positioned in substantially the same position as the lens which has been removed.

It is yet a further object of the present invention to provide such a lens implant procedure which can be used for implanting lenses of varying types, sizes and shapes, including human and animal lenses.

It is yet another object of the present invention to provide a lens implant procedure which avoids the use of sutures and which minimizes the number and types of foreign substances implanted within the eye.

It is still a further object of the present invention to provide a variable focus lens for use with the aforesaid procedure.

It is still an additional object of the present invention to provide an instrument for use with such a procedure which facilitates the removal of the diseased lens and the insertion of the new lens.

Various other objects and advantages of the present invention will become clear from the following detailed description of several exemplary embodiments thereof, and the novel features will be particularly pointed out in conjunction with the claims appended hereto.

SUMMARY OF THE INVENTION

In accordance with the teachings of the present invention, a method of replacing a lens has, as a first step, the displacement of the cornea and conjunctiva to provide access to the iris. The iris is then positioned to provide access to the anterior lens capsule. A generally horizontal capsulotomy incision is performed in the anterior lens capsule. The superior portion of the capsular incision is folded back to expose the apex of the lens. A first portion of a removal tool is inserted between the anterior lens capsule and the anterior surface of the lens while inserting a second portion of the removal tool between the posterior lens capsule and the posterior surface of the lens. The lens is then grasped with the first and second portions of the removal tool and rotated to dislodge it from the capsule and partially remove it from the capsule. The lens is then removed while the capsule is kept open. A replacement lens is then inserted into the capsule, the tool is withdrawn from the capsule, and the superior capsule flap, the iris the cornea and the conjunctiva are all repositioned.

The novel tool for use in accordance with the foregoing method includes a tweezer body having a normally open position and first and second ends. Gripping means are mounted to the first and second ends, which gripping means are substantially circular and have concave inner surfaces facing each other and convex outer surfaces. The concave inner surfaces are constructed and arranged to grasp a lens.

The novel implant lens of the present invention is formed from inert, non-toxic materials and is sufficiently flexible so that its focus may be varied by constriction and relaxation of ciliary muscles.

The invention will be more fully understood by reference to the following detailed description of several exemplary embodiments thereof in conjuction with the accompanying drawings in which:

FIG. 1 is a side sectional view of an eye during the implant procedure illustrating the removal tool wherein the first gripping means has been inserted into the lens capsule against the anterior surface of the lens while the second gripping means of the removal tool has been inserted against the posterior surface of the lens;

FIG. 2 is a side sectional view similar to FIG. 1 showing an erisophake being used to remove the lens from the capsule;

FIG. 3 is a side sectional view similar to FIG. 1 showing the capsule being kept open by the first and second gripping means of the removal tool;

FIG. 4 is a side sectional view similar to FIG. 1 showing the new lens being inserted by means of an erisophake;

DESCRIPTION OF THE PREFERRED EMBODIMENT

Figure 5:
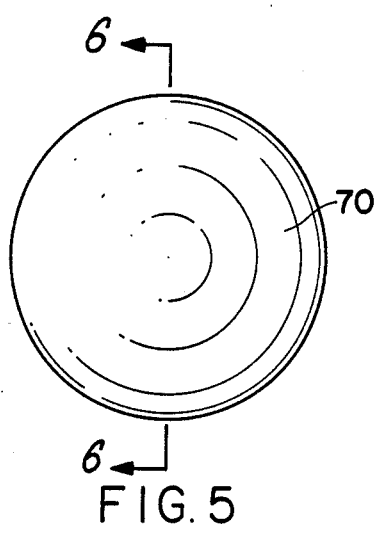
FIG. 5 is a front elevational view of a convex artificial lens of the present invention.

Referring now to the drawings wherein like reference numerals designate like parts throughout the several views, FIGS. 1-4 represent, in that order, several of the stages of the surgical procedure of the present invention. The patient's eye is represented generally by reference numeral 10.

The procedure begins with a 10 o'clock to 2 o'clock superior corneal incision and conjunctival flap which allows for the cornea 12 and the conjunctiva 14 to be displaced from the area directly in front of the lens and to provide access to the iris 16. At this time, it is necessary to position the iris 16 to provide access to the anterior lens capsule 18. This can be accomplished with a 12 o'clock complete iridectomy. Alternatively, the iris may be dilated if complete dilation can be accomplished. The iris 16 is then moved aside by means of a suture or an iris forceps.

The next step in the procedure is the performance of a generally horizontal capsulotomy incision in the anterior lens capsule 18. The capsulotomy is located approximately three millimeters below the apex of the anterior capsule 18 and extends from left to right from about the 10 o'clock position to about the 2 o'clock position.

The removal tool 50 of the present invention, which is illustrated in FIGS. 10-14, should be used at this stage of the procedure. The tool 50 has a tweezer body 52 with a normally open position, so that a squeezing force is required to bring the two arms thereof together.

Figure 10:
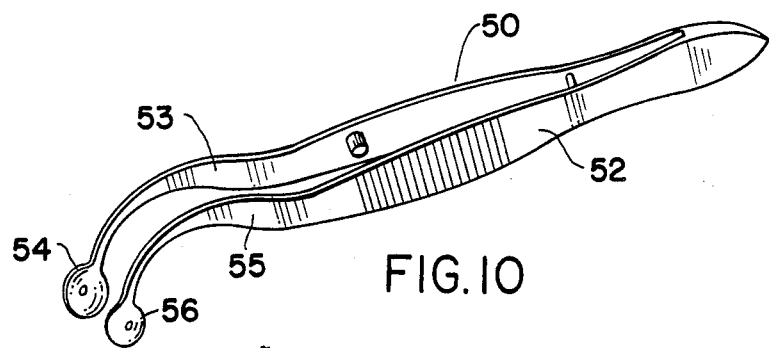
FIG. 10 is an isometric view of a removal tool of the present invention.
Figure 11:
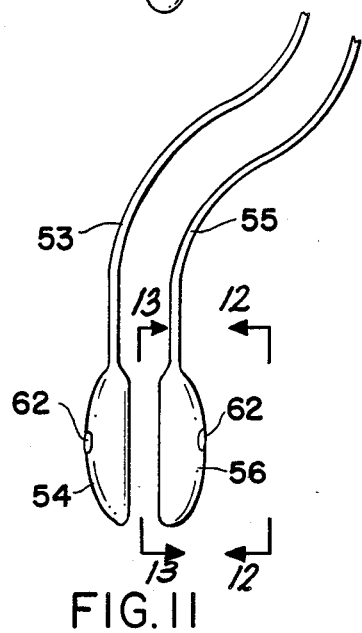
FIG. 11 is a partial left side elevational view of the gripping means of the removal tool.
Figure 12:
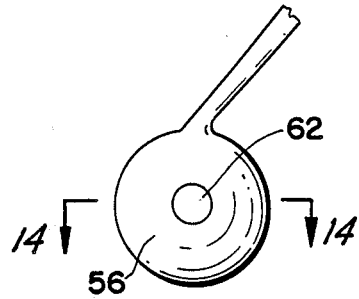
FIG. 12 is a view taken along the line 12—12 in FIG. 11 and looking in the direction of the arrows.
Figure 13:
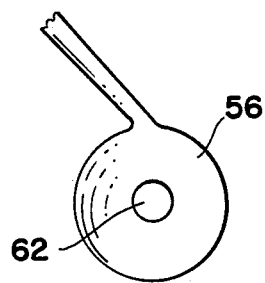
FIG. 13 is a view taken along the line 13—13 in FIG. 11 and looking in the direction of the arrows.
Figure 14:
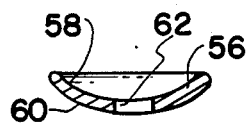
FIG. 14 is a top sectional view taken along the line 14—14 in FIG. 12 and looking in the direction of the arrows.

The removal tool 50 has gripping means mounted to each of the end, as best illustrated in FIG. 10. These gripping means consist of first and second saucer-shaped members 54, 56. The saucer-shaped members 54, 56 have a substantially circular shape as can be best appreciated from FIG. 12 and 13. Additionally, as can be best seen in FIG. 14, each of the saucer-shaped members 54, 56 has a concave inner surface 58 and a convex outer surface 60. The saucer-shaped members 54, 56 also have a central opening 62. The saucer-shaped members 54, 56 are connected to the tweezer body 52 through curved offset portions 53, 55.

The removal tool 50 preferably has an overall length of approximately three inches. The saucer-shaped members 54, 56 preferably have a diameter of approximately four millimeters and a "saucer" depth of approximately two millimeters. The central opening 62 should have a diameter of approximately one millimeter. The central opening 62 serves the function of releasing entrapped fluid or air between the tool and the lens.

Returning now to the surgical procedure of the present invention, and referring to FIG. 1, after the capsulotomy is performed, the removal tool 50 is used to fold back the superior portion of the capsular incision. In particular, the saucer-shaped member 54 is inserted between the posterior lens capsule 20 and the posterior surface of the lens 22, which has the effect of exposing the apex of the lens 22. The outer saucer-shaped member 56 is inserted between the anterior lens capsule 18 and the anterior surface of the lens 22. The tool 50 is then squeezed so that the two saucer-shaped members grip the lens 22. The tool 50 is then manipulated by hand so as to rotate the lens 22 from clockwise and counterclockwise to dislodge the lens 22 from the capsule. The lens 22 is then lifted approximately half way out of the capsule with the removal tool 50.

AT this time, an erisophake 26 is used to remove the lens 22 totally from the capsule. The squeezing pressure on the tweezer body 52 of the removal tool 50 is slightly released to keep the capsule open. The interior of the lens capsule is then irrigated with sterile saline solution. Thereafter, any capsular plaque is removed by means of suction.

A new lens 22' may then be implanted well into the capsule with an erisophake 26. The lens implant 22' should be a suitable transparent, flexible, biologically inert, non-toxic, non-irritating material which is not susceptible to absorption by body fluids. Once the new lens 22' is seated well into the capsule, the removal tool 50 can be withdrawn.

The superior capsule flap is then repositioned, as well as the iris 16. The anterior chamber of the eye is then irrigated. The corneal incisions and the conjunctival flaps are closed by means of sutures. Thereafter, distention of the anterior chamber takes place by means of air or fluid.

It will be appreciated by those skilled in the art that post-operative medication such as neo-decadron ophthalmic ointment should be used to counteract infection and to promote healing. Additionally, a cycloplegic such as cyclopentolate should be instilled before the effects of local or general anesthesia wear off. The cyclopegic should be continued for a period of approximately one to two weeks.

It will be appreciated that, with the procedure just described, it is possible to implant a natural human or animal lens within the human lens capsule, which will be totally surrounded by the lens capsule. The capsule, is turn, is held in position by the natural zonular fibers attached to the ciliary muscle. The change in contour and focus of the lens is accomplished by the natural constriction and relaxation of the ciliary muscles applying pressure to the lens implant.

The present invention may also be used with an artificial lens and, in particular, a soft or flexible lens. Such a flexible lens can be made of the same type of material presently being used for external contact lenses such as HEMMA (hydrophilic plastic), M.M.A. (soft plastic), silicone (hard and soft plastic) and P.M.M.A. (hard plastic), with M.M.A. being the preferred material.

Figure 6:
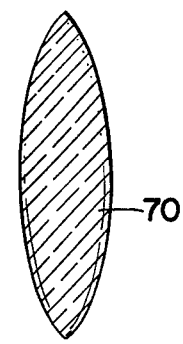
FIG. 6 is a cross-sectional view taken along the line 6-6 in FIG. 5 and looking in the direction of the arrows.
Figure 7:
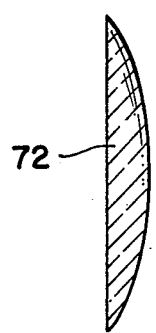
FIG. 7 is a cross-sectional view of a plano-convex lens of the present invention.
Figure 8:
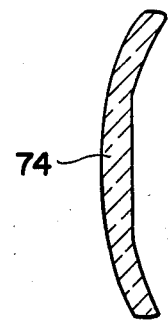
FIG. 8 is a cross-sectional view of a modified plano-convex lens of the present invention.
Figure 9:
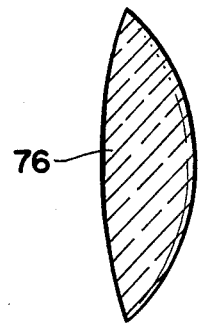
FIG. 9 is a cross-sectional view of a bi-convex lens of the present invention.

It should also be appreciated that the implanted lens 22' of the present invention, whether flexible (and thus having a variable focus) or rigid (and thus having a fixed focus) may have a variety of sizes and shapes. Thus, FIG. 5 and 6 illustrate a convex lens 70 in plan view and in cross-sectional view respectively. FIG. 7 illustrates a plano convex lens 72; FIG. 8 illustrates a modified plano-convex lens 74; and FIG. 9 illustrates a bi-convex lens 76. The lens 22' should be approximately nine millimeters to thirteen millimeters in diameter and have a thickness of approximately 3.0 to 4.5 millimeters, all of which dimensions are variable depending upon the lens power required, the material used and the physical and anatomical limitations of the particular eye and the lens capsule.

It will thus be appreciated that the present invention provides virtually complete and natural vision performance of the human or animal eye, since it utilizes the natural lens capsule (rather than destroy it or mutilate it), as well as the surrounding ciliary muscles and natural zonular fibers. It totally avoids the use of sutures, wedges, prongs and riveting devices which have a tendency to apply constant pressure and trauma to the surrounding tissue, thus causing irritation and inflammation.

As will be readily apparent to those skilled in the art, the invention may be used in other specific forms without departing from its spirit or essential characteristics. The present embodiments are, therefore, to be considered as illustrative and not restrictive, the scope of the invention being indicated by the claims rather than the foregoing description, and all changes which come within the meaning and range of equivalence of the claims are therefore intended to be based therein.

What is claimed is:

1. A method of replacing a lens comprising:
   (a) displacing the cornea and the conjunctiva to provide access to the iris;
   (b) positioning the iris to provide access to the anterior lens capsule;
   (c) performing a generally horizontal capsulotomy incision in the anterior lens capsule;
   (d) folding back the superior portion of the capsular incision to expose the apex of the lens;
   (e) inserting a first portion of a removal tool between the anterior lens capsule and the anterior surface of the lens while inserting a second portion of said removal tool between the posterior lens capsule and the posterior surface of the lens;
   (f) grasping the lens with said first and second portions of said removal tool and rotating the lens to dislodge it from the capsule and partially remove it from the capsule;
   (g) removing the lens while keeping the capsule open;
   (h) inserting a replacement lens into the capsule;
   (i) withdrawing said removal tool from the capsule; and
   (j) repositioning the superior capsule flap, the iris, the cornea and the conjuctiva.

2. A method according to claim 1 wherein said displacement step consists of a 10 o'clock to 2 o'clock superior corneal incision and conjunctival flap.

3. A method according to claim wherein said positioning step consists of a 12 o'clock complete iridectomy.

4. A method according to claim 1 wherein said positioning step consists of a dilation of the iris.

5. A methoid according to claim 1 wherein said capsulotomy is from the 10 o'clock position to the 2 o'clock position.

6. A method according to claim 1 wherein said capsulotomy is performed approximately three millimeters from the apex of the capsule.

7. A method according to claim 1 wherein said removing step is done with an erisophake 8. A method according to claim 1 or claim 7 wherein during said removing step the capsule is kept open with said removal tool.

9. A method according to claim 1 further comprising the step of irrigating the lens capsule after said removing step.

10. A method according to claim 1 further comprising the step of removing subcapsular plaque after said removing step.

11. A method according to claim 1 wherein said replacement lens is a human lens transplant.

12. A method according to claim 1 wherein said replacement lens is an animal lens transplant.

13. A method according to claim 1 wherein said replacement lens is an artificial lens transplant.

14. A method according to claim 13 wherein said artificial lens has a variable focus.

15. A method according to claim 14 wherein said lens is made of flexible material.

* * * * *